United States Patent [19]
Komuro

[11] Patent Number: 5,193,236
[45] Date of Patent: Mar. 16, 1993

[54] MAGNETIC PILLOW

[75] Inventor: Mitsuo Komuro, Tokyo, Japan

[73] Assignee: Nippon Athletic Industry Company, Tokyo, Japan

[21] Appl. No.: 928,640

[22] Filed: Aug. 14, 1992

Related U.S. Application Data

[63] Continuation of Ser. No. 666,073, Mar. 7, 1991, abandoned.

[51] Int. Cl.$^5$ .............................................. A47C 20/02
[52] U.S. Cl. .......................................... 5/636; 5/481; 5/906
[58] Field of Search .................... 5/481, 630, 631, 638, 5/643, 645, 639, 448, 906

[56] References Cited

U.S. PATENT DOCUMENTS

| | | | |
|---|---|---|---|
| 2,917,046 | 12/1959 | Fairbanks | 5/434 |
| 3,287,750 | 11/1966 | Jessup | 5/481 |
| 4,143,435 | 3/1979 | Masuda | 5/481 |
| 4,207,636 | 6/1980 | Ceriani | 5/434 |
| 4,330,892 | 5/1982 | Fukushima | 5/437 |
| 4,649,582 | 3/1987 | Cho | 5/434 |
| 4,686,724 | 8/1987 | Bedford | 5/481 |
| 4,777,855 | 10/1988 | Cohen | 5/434 |
| 4,850,068 | 7/1989 | Walpin | 5/434 |
| 4,924,542 | 5/1990 | Yamaguchi | 5/481 |

Primary Examiner—Renee S. Luebke
Assistant Examiner—Flemming Saether
Attorney, Agent, or Firm—Young & Thompson

[57] ABSTRACT

A health pillow having both magnetic effect and manual pressure effect and further having good air permeability, which comprises a hollow pillow body consisting of a foamed synthetic resin; a large number of permanent magnets distributedly arranged on the upper surface of the pillow body; and a cover material covering the pillow body and the permanent magnets. The said hollow pillow body has a large number of projections, which consist of the foamed synthetic resin itself and are distributedly arranged on its upper surface such that each permanent magnet is arranged between the projections, and further has a large number of projections consisting of the foamed resin itself distributedly arranged on its bottom surface. The hollow pillow body further has vent holes distributedly formed so as to communicate the outside of the hollow pillow body with the hollow portion formed inside the body.

3 Claims, 6 Drawing Sheets

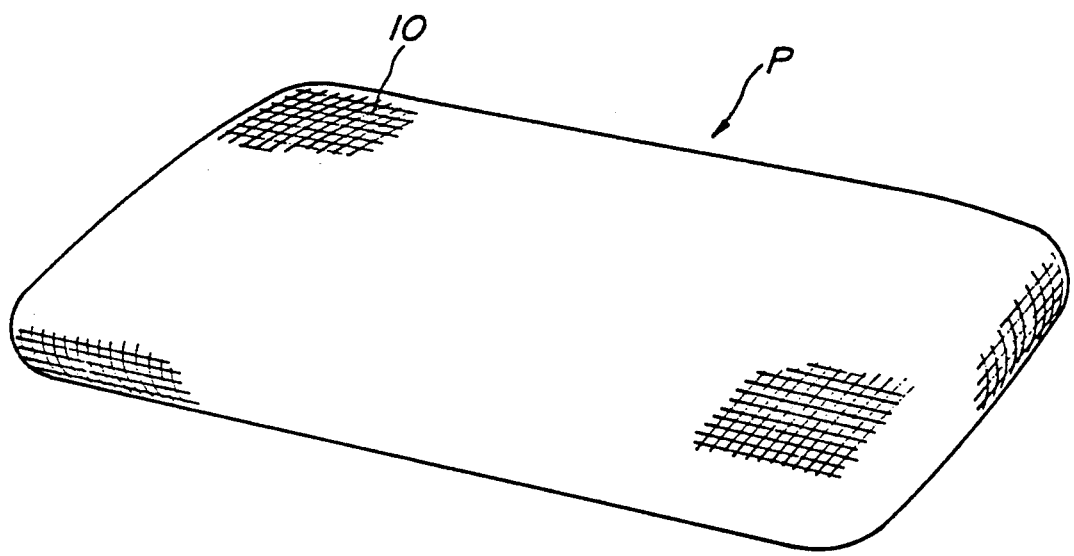
FIG_1

FIG._2
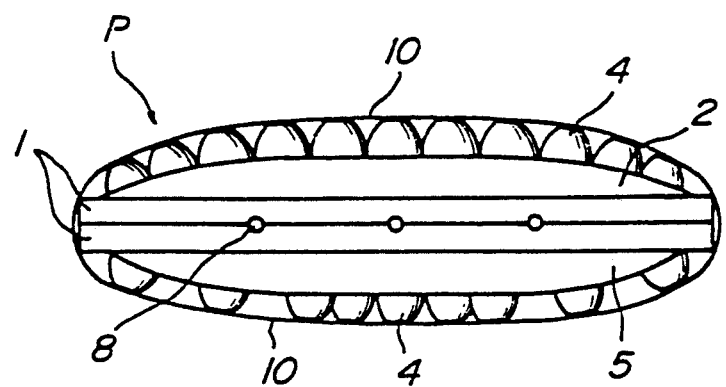
FIG._3
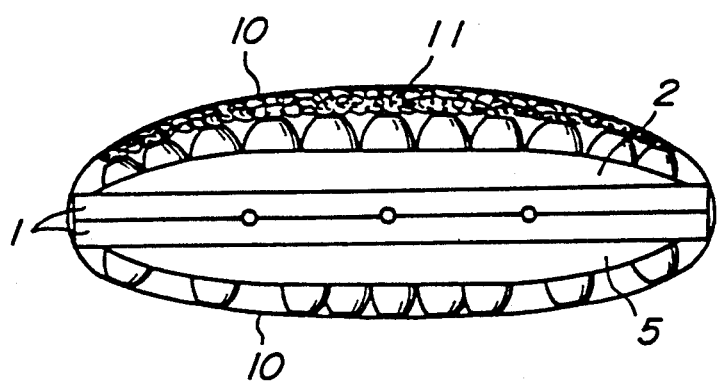

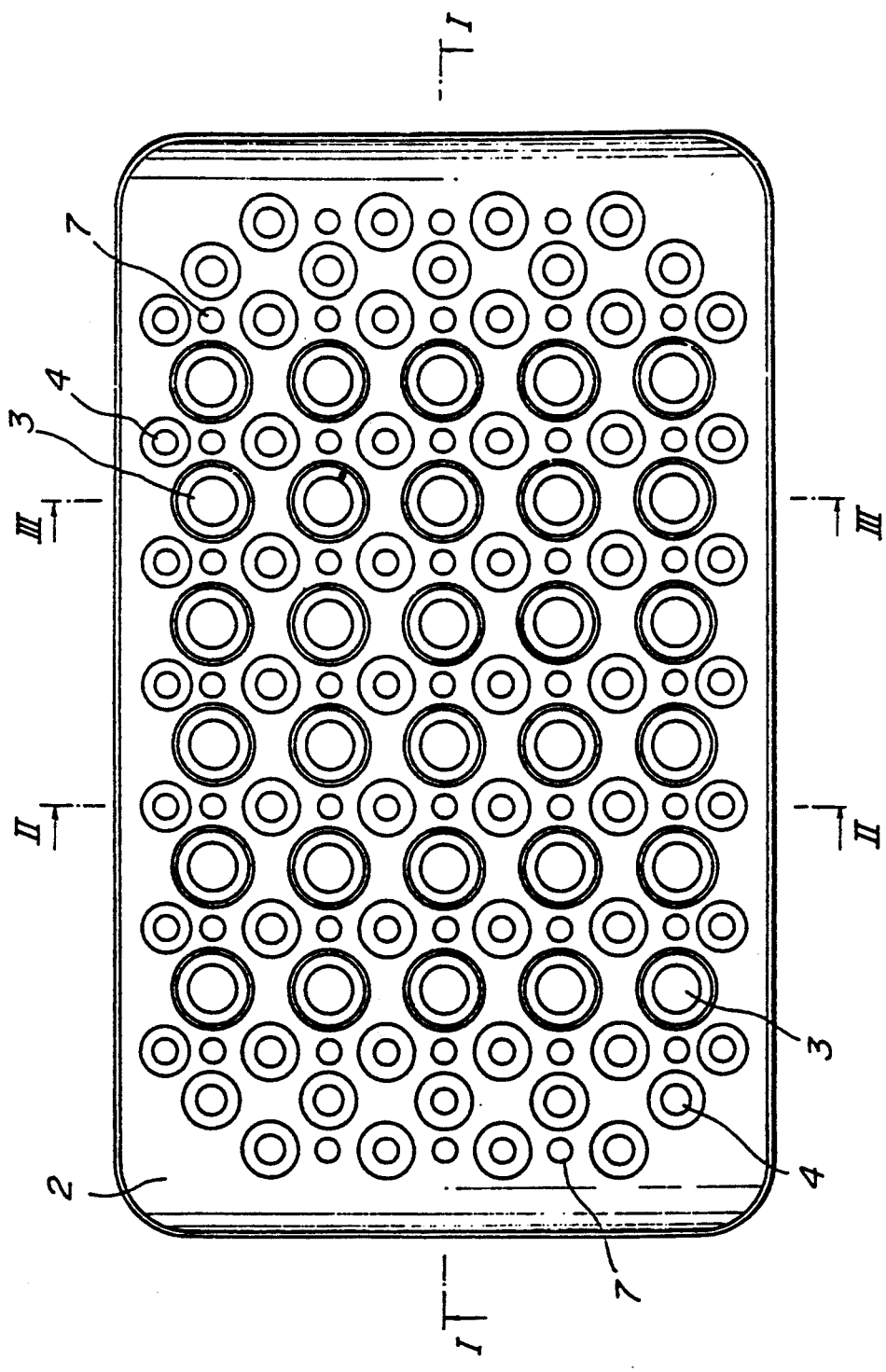

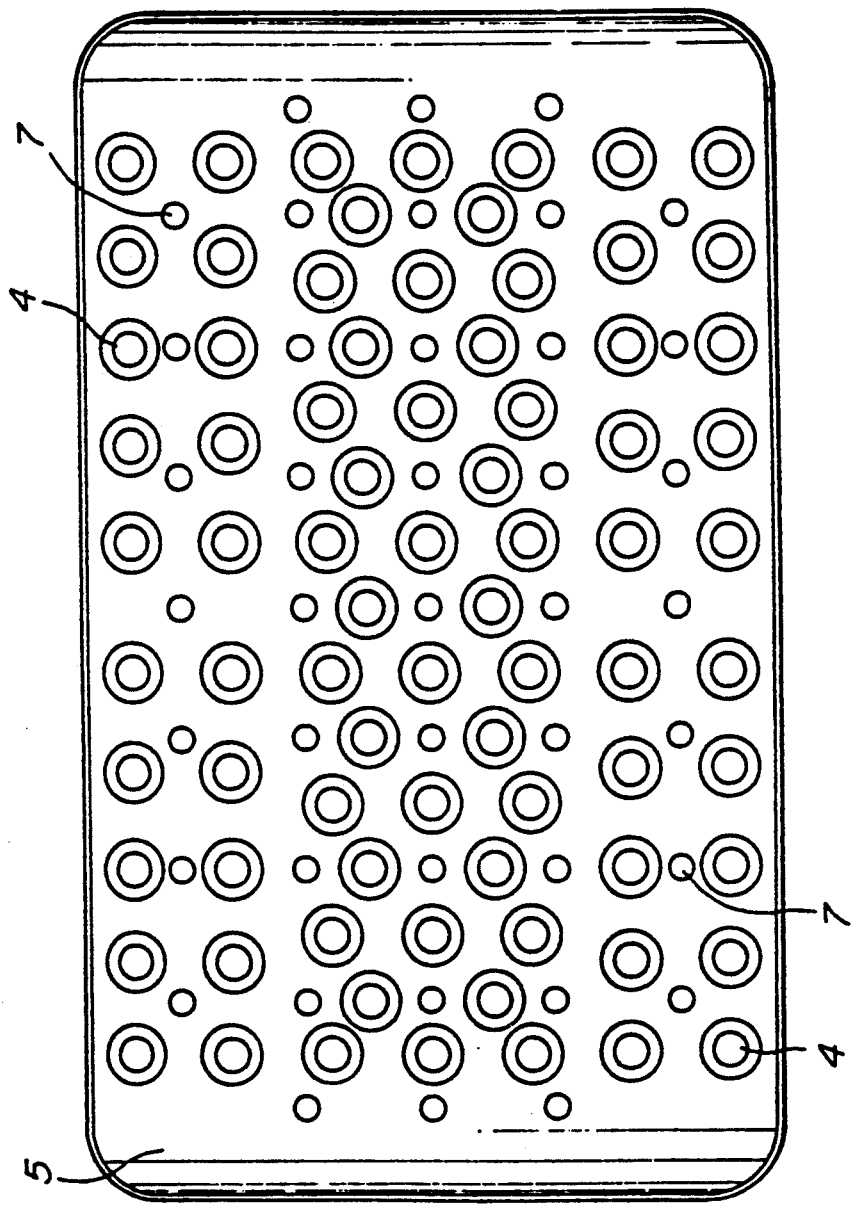

FIG_6
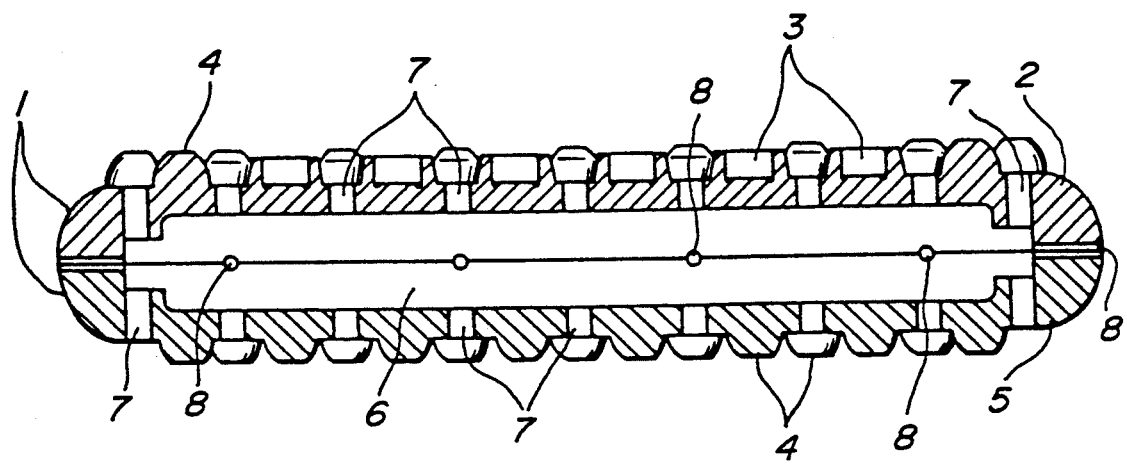
FIG_7
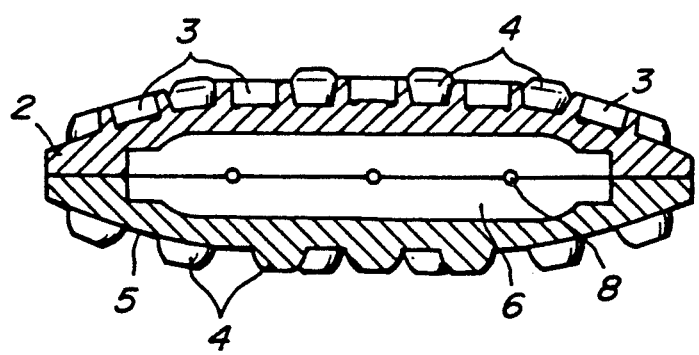

FIG_8
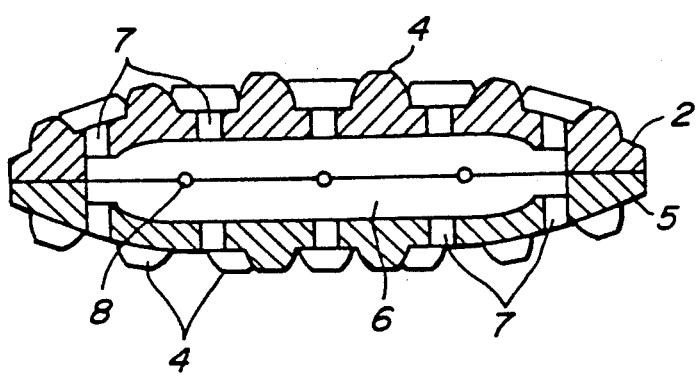
FIG_9
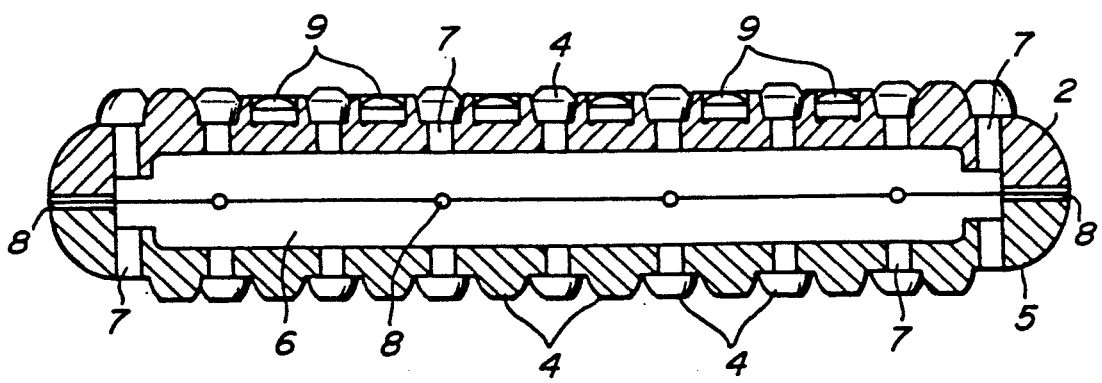

MAGNETIC PILLOW

This application is a continuation of application Ser. No. 07/666,073, filed Mar. 7, 1991, now abandoned.

BACKGROUND OF THE INVENTION

1. Field of the Invention

This invention relates to a health pillow having a magnetic effect due to the magnetic lines of force of magnets and a manual pressure effect and further having a good air permeability.

2. Related Art Statement

There have been proposed various kinds of pillows for a long time, but it has not been possible to produce inexpensively a light-weight pillow having a magnetic effect and a manual pressure effect and further having a good air permeability.

SUMMARY OF THE INVENTION

The object of the present invention is to solve the above described problems.

One of the features of the present invention lies in a magnetic pillow comprising a hollow pillow body consisting of a foamed synthetic resin; a large number of permanent magnets distributedly arranged on the upper surface of the pillow body; and a cover material covering the pillow body and the permanent magent; said hollow pillow body having a large number of projections, which consist of the foamed synthetic resin itself and are distributedly arranged on its upper surface such that each permanent magnet is arranged between the projections, and further having a large number of projections consisting of the foamed synthetic resin itself and being distributedly arranged on its bottom surface; and said hollow pillow body further having a large number of vent holes distributedly formed so as to communicate the outside of the hollow pillow body with the hollow portion formed inside the body.

Another feature of the present invention lies in a magnetic pillow, wherein the above described magnetic pillow further comprises a cotton interposed between the hollow pillow body and the cover material, said cotton having deodorizing and antibiotic properties.

BRIEF DESCRIPTION OF THE DRAWING

FIG. 1 is a perspective view illustrating the external appearance of one embodiment of the magnetic pillow according to the present invention;

FIG. 2 is a side view of the pillow illustrated in FIG. 1, illustrating its cover material by a cross-section;

FIG. 3 is a side view of another embodiment of the magnetic pillow according to the present invention, illustrating its cover, material by a cross-section similarly to FIG 2;

FIG. 4 is a plan view of the pillow body of a magnetic pillow according to the present invention;

FIG. 5 is a bottom view of the pillow body of a magnetic pillow according to the present invention;

FIG. 6 is a cross-sectional view of the pillow body illustrated in FIG. 4 in the arrow direction along the line 6—6 in FIG. 4;

FIG. 7 is a cross-sectional view of the pillow body illustrated in FIG. 4 in the arrow direction along the line 7—7 in FIG. 4;

FIG. 8 is a cross-sectional view of the pillow body illustrated in FIG. 4 in the arrow direction along the line 8—8 in FIG. 4; and FIG. 9 is a view similar to FIG. 6 but with permanent magnets fixed thereto.

DESCRIPTION OF THE PREFERRED EMBODIMENT

One embodiment of the present invention will be explained referring to the accompanying drawings.

In this embodiment, a pillow body 1 is made of a foamed synthetic resin, for example, foamed crosslinked polyethylene or the like, has a hollow portion 6 formed inside the body 1, and consists of two parts of an upper-half pillow body 2 and a lower-half pillow body 5. The upper-half pillow body 2 has a large number of hollow cylindrical recesses 3, each for receiving a permanent magnet 9 therein, formed by projecting and distributedly arranging the foamed synthetic resin itself on its upper surface, and further has a large number of semi-spherical projections 4 consisting of the foamed synthetic resin itself and being distributedly arranged on its upper surface such that each hollow cylindrical recess 3 is arranged between the projections 4. The lower-half pillow body 5 has a large number of semi-spherical projections 4 consisting of the foamed synthetic resin itself and being distributedly arranged on its bottom surface. Further, the upper-half pillow body 2 has a large recess opening downwardly and occupying the major portion of its inside, and the lower-half pillow body 5 has a large recess opening upwardly and occupying the major portion of its inside such that a hollow portion 6 is formed between the superposed upper-half and lower-half pillow bodies 2 and 5. A large number of vent holes 7 and 8 are distributedly formed so as to communicate the outside of the upper-half and lower-half pillow bodies 2 and 5 with the hollow portion 6.

That is, the vent holes 7 are formed in each of the upper-half pillow body 2 and the lower-half pillow body 5, and the vent holes 8 are formed at the abutting interface of the upper-half pillow body 2 with the lower-half pillow body 5.

A permanent magnet 9 (refer to FIG. 9) having an upper surface previously formed into a convex spherical shape is inserted into and fixed to each of the above described hollow cylindrical recesses 3 formed in the upper-half pillow body 2, and this upper-half pillow body 2 having permanent magnets 9 fixed thereto is superposed on the lower-half pillow body 5, and the resulting assembly is covered with a cover material 10 (refer to FIGS. 1 and 2), such as cloth or the like, to obtain a magnetic pillow P according to the present invention.

Further, a layer of deodorizing and antibiotic cotton 11 (for example, Saniter (trademark) sold by Kuraray Co., Ltd., or Biosil (trademark) sold by Toyo Boseki Co., Ltd.) having deodorizing and antibiotic properties can be interposed between the upper-half pillow body 2 and the cover material 10 of the above described magnetic pillow P as illustrated in FIG. 3.

When the magnetic pillow P having the above described structure according to the present invention is used, the magnetic lines of force of a large number of the permanent magnets 9, which are distributedly and projectingly arranged on the upper surface of the upper-half pillow body 2, acts on the human body to give a magnetic effect thereto, and at the same time there can be obtained a manual pressure effect caused by press-contacting a human body with a large number of both of these permanent magnets 9 and the projections 4 distributedly arranged on the upper surface of the upper-half pillow body 2 such that each permanent magnet 9 is arranged between the projections 4.

Moreover, the magnetic pillow P of the present invention has a very high air permeability due to the presences of a large number of the vent holes 7 and 8, the hollow portion 6 formed inside the pillow body 1, and a large number of the projections 4 distributedly arranged on the outer surface of the pillow body 1.

As described above, according to the present invention, the hollow pillow body 1 is made of a foamed synthetic resin, and hence a very light-weight magnetic pillow P can be inexpensively mass-produced.

Further, the magnetic pillow P of the present invention has a large number of permanent magnets 9 distributedly arranged on the upper surface of the upper-half pillow body 2 of the pillow body 1 and a large number of projections 4 consisting of the foamed synthetic resin itself and being distributedly arranged on the upper surface of the upper-half pillow body 2 such that each permanent magnet 9 is arranged between the projections 4, and further has a large number of projections 4 consisting of the foamed synthetic resin itself and being distributedly arranged on the bottom surface of the lower-half pillow body 5. Therefore, the magnetic pillow P of the present invention has both a magnetic effect and a manual pressure effect.

Further, in the magnetic pillow P of the present invention, there are a large number of vent holes 7 and 8, which communicate the outside of the above described upper-half and lower-half pillow bodies 2 and 5 with the hollow portion 6, and hence the magnetic pillow P has a high air permeability and can suppress effectively the increasing of moisture and the raising of temperature during sleep.

When cotton 11 having deodorizing and antibiotic properties is interposed between the upper-half pillow body 2 and the cover material 10 in the above described magnetic pillow P, the cotton 11 acts to soften the contact feeling of a human body with the above described permanent magnets 9 and projections 4 and further exhibits deodorizing and antibiotic effects. Therefore, the use of cotton 11 having deodorizing and antibiotic properties in the magnetic pillow of the present invention can remove offensive odors and is good for health.

As described above, the magnetic pillow of the present invention has excellent effects in practical use.

What is claimed is:

1. A magnetic pillow comprising a hollow pillow body consisting of a foamed synthetic resin; a large number of permanent magnets distributedly arranged on the upper surface of the pillow body; there being hollow cylindrical recesses on the upper surface of said pillow body and said permanent magnets being inserted in and fixed only to the foamed synthetic resin within said recesses; and a cover material covering the pillow body and the permanent magnets; said hollow pillow body having a large number of projections, which consist of the foamed synthetic resin itself and are distributedly arranged on its upper surface such that each recess is arranged between the projections, and further having a large number of projections consisting of the foamed synthetic resin itself and being distributedly arranged on its bottom surface, and said hollow pillow body further having a large number of vent holes distributedly formed so as to communicate the outside of the hollow pillow body with the hollow portion formed inside the body, said magnets having convex upper surfaces and cotton interposed between the hollow pillow body and the cover material, said cotton having deodorizing and antibiotic properties.

2. A magnetic pillow according to claim 1, wherein said convex upper surfaces of said magnet are of spherical shape.

3. A magnetic pillow as recited in claim 1, wherein said upper surfaces of said magnetic are disposed lower than the uppermost portions of said projections.

* * * * *